United States Patent
Epping

Patent Number: 5,266,900
Date of Patent: Nov. 30, 1993

[54] METHOD AND APPARATUS FOR DETERMINING ELECTRICAL CHARGE CHARACTERISTICS OF TONER MATERIALS

[75] Inventor: Reinhold H. Epping, Neufahrn, Fed. Rep. of Germany

[73] Assignee: Epping GmbH, Neufahrn/Munich, Fed. Rep. of Germany

[21] Appl. No.: 586,487

[22] Filed: Sep. 21, 1990

[51] Int. Cl.$^5$ .................. G03G 21/00; G01N 27/60
[52] U.S. Cl. ..................... 324/452; 355/246
[58] Field of Search ............ 324/452, 457, 464, 459; 364/555; 355/246; 73/23.37, 23.41

[56] References Cited

U.S. PATENT DOCUMENTS

| | | | |
|---|---|---|---|
| 3,757,999 | 9/1973 | Maksymiak | 355/246 |
| 3,779,204 | 12/1973 | Altmann | 324/72 |
| 3,999,119 | 12/1976 | Bares | 324/454 |
| 4,026,643 | 5/1977 | Bergman | 355/246 |
| 4,079,266 | 3/1978 | Vipond | 355/246 |
| 4,375,673 | 3/1983 | Lewis et al. | 364/555 |
| 4,706,032 | 11/1987 | Allen et al. | 324/678 |

FOREIGN PATENT DOCUMENTS 3338139  5/1985  Fed. Rep. of Germany.

OTHER PUBLICATIONS

R. H. Epping et al., "Standardized Measurements Methods for Analyzing Electrostatically Charged Toners", SPIE, vol. 1252, pp. 123-131, *Hard Copy and Printing Technologies* (1990).

R. H. Epping et al., "Electrical Charge and Conductivity Measurement with Modern Mono-Component Developers", *Electrophotography*, vol. 27, No. 4, (1988).

R. H. Epping, "Lifetime Simulation and Charge Related Parameters of Two Component Developers", *The Fourth International Congress on Advances in Non-Impact Printing Technologies*, Mar. 20-25, 1988, pp. 102-112, New Orleans, Louisiana.

*Primary Examiner*—Jack B. Harvey
*Assistant Examiner*—Maura K. Regan
*Attorney, Agent, or Firm*—Townsend and Townsend

[57] ABSTRACT

The electrostatic quality of toner material is measured by introducing the toner material into a measuring cell so that it flows through an opening in the measuring cell into a receiving chamber that is substantially free of gas flows and collects on a charged electrode disposed within the receiving chamber. The quantity of toner material collected on the electrode is utilized as an index of the quality of the toner material with respect to its electrostatic charge capability. In addition, the dispersal profile of the toner material collected on the electrode may be utilized for analytic purposes.

33 Claims, 4 Drawing Sheets

METHOD AND APPARATUS FOR DETERMINING ELECTRICAL CHARGE CHARACTERISTICS OF TONER MATERIALS

The present invention relates to a method and an apparatus for determining electrical charge characteristics of toner materials.

The analysis of the physical condition of toner materials, such as developers used in copiers, printers and the like, generally requires time, much technical expenditure and occasional limited modification of the equipment. The knowledge of changes in time and place in the condition of the developer in the development zone of a copier is, however, essential for understanding the proceedings with electrostatic picture reproductions. A basic knowledge of the developing process is most important for the construction of a copier or the like.

To compare different toner materials and developers it is of great advantage to determine the physical parameters by use of test units which are easy to handle. The concept of suitable testing conditions suggests the development of standardized methods to make it possible to compare decisive criteria of different toner materials. This is particularly important for determining the electrostatic charge of developers.

In order to obtain similar charging conditions of toner materials used in copiers, the parameters occurring in copiers have to be simulated, since the electrostatic charge of the toner material in electrographic copiers depends on the following conditions:

1. Toner Material Parameter
   chemical composition
   one or multi-component toner materials of developers
   surface conditions
   electric conductivity
2. Activation Parameter
   frequency of collisions between toner particles and with their surroundings
   intensity of collisions
   mixing speed in multi-component developers
3. Outside Parameters
   electric field
   magnetic field
   interactions with ambient materials (walls, electrodes, climate conditions).

In this context it is also essential, especially when determining the electrostatic qualities of relatively coarse toner starting materials, to grind or pulverize such material in order to obtain the most accurate production-oriented data possible. Under normal processing conditions such starting material consists initially of particles with average grain size ranging from 0.8 mm to approximately 2 mm which are then finely ground to a granular size of 1 to 50 $\mu$m when being processed as toner for use in copiers. Special pulverizing methods have been developed for industrial purposes in which in particular so-called jet mills for pulverizing toner starting material are currently being employed. In this case pulverization of the material is achieved with the aid of jets of pressurized air. These are injected or discharged at a high velocity into a cylindrical grinding chamber, creating a spiral air flow, in which the blown or injected grinding material is pulverized through collision of the individual particles with one another. Further, in counter-jet mills, pulverization is achieved by introducing particles being pulverized into crossing air flows and causing them to collide against one another at a high velocity.

For laboratory purposes it is not feasible to employ an industrial-type jet mill for pulverizing toner material. Nevertheless, it is desirable to simulate such pulverization on a laboratory scale, in order to achieve the most realistic pulverization of toner material by employing procedures that closely resemble the actual industrial processes used.

DESCRIPTION OF RELATED ART

By way of example, an industrially employed, fluidized bed type-counter jet mill is shown in German Patent No. DE PS 3,338,138 C2, which is also suited for, among other things, pulverizing toner material.

From U.S. Pat. No. 4,375,673, an apparatus and a method for measuring the distribution of toner particles as a function of the size and charge thereof are known. The toner particles, which have been blown off from the carrier, are transported through a narrow guide pipe into a tube with laminar air flow (x-axis). By means of two electrodes an electric field, which is in a vertical position to the air flow (y-axis), deflects the toner particles proportional to the charge/diameter-value of a toner particle away from the original line of flow. The toner is collected as a toner-charge/diameter-spectrum vertical to the flow direction on a filter.

R. H. Epping, M. Munz and M. Mehlin, in *Electrophotography*, Vol. 27, No. 4 (1988), pages 528–532, describe electrical charge and conductivity measurements with modern mono-component developers. The blown-off toner material is transported from a measuring cell into a laminar air flow inside a tube, wherein the toner material at once gets the same speed as the laminar air flow. Cross-linked to the air flow, an electrical field is applied for moving the toner to a registration electrode, which collects the toner particles. Due to the dynamic equation of the toner particles, all particles with constant ratio q/d (charge/diameter) deposit as a toner spectrum line, depending on the deflection of the toner in direction of the laminar air flow. For good electrostatic charging conditions, the toners are activated by a rotating magnetic field generated by a pair of two cross-linked magnets, thus simulating a magnetic brush station of a copier.

In the prior art apparatus and methods for measuring the distribution of toner particles as a function of the size and charge thereof, the measuring results depend greatly on the nature and method of treating the powder of the toner materials. The resultant values are influenced not only by the type of movement and contact conditions of the individual particles to each other, called "activation," but also by marginal conditions such as material and geometry of the developing space, frequency and polarization direction of the electromagnetic field, temperature and relative humidity.

In addition, heretofore known methods and apparatus for determining electric charge characteristics of toner materials have proven to be relatively complex and correspondingly expensive, both in construction and in operation.

SUMMARY OF THE INVENTION

In accordance with the invention, the electrostatic quality of toner material useful for electrostatic copiers and printers which is submitted in sample quantities for testing, is determined by measurements related to accumulations on a charged electrode. Toner material introduced into a measuring cell flows through an opening in the measuring cell into a receiving chamber that is substantially free of gas flows and collects on a polarized electrode disposed within the chamber. The quantity of toner material collected on the electrode is utilized as an index of the quality of the toner material with respect to its electrostatic charge capability. In addition, the dispersal profile of the toner material collected on the electrode may be utilized for analytic purposes. Specifically, toner quality is determined by measurement using only one integral dimension with respect to the quantity ratio of both charges present in the toner material. A method according to a specific embodiment of the present invention for determining the electrical charge characteristics of any type of toner material, comprises the steps of:

introducing the toner material into a measuring cell;

allowing the toner material to flow from an opening in the measuring cell into a receiving chamber that is substantially free of gas flows;

allowing the inflowing toner material to collect on an electrode disposed within the receiving chamber to which a voltage with a predetermined polarity is applied;

measuring over a certain time frame the quantity of toner material that enters the receiving chamber and collects on the electrode; and defining the electrical charge characteristics of the toner material as a function of the measuring results.

In a preferred embodiment of the present invention the measurement is duplicated, but with a voltage of an alternate polarity is applied to the electrode. Hence, by defining electrical properties as a function of the difference in quantities of toner material that collect on the electrode when voltages of opposite polarity are applied, an index for the quality of the toner material is obtained.

An object of the present invention is therefore to develop a method for determining electrical charge characteristics of toner material which can be employed with greater facility and efficiency, but which also allows one to make sufficiently accurate and precise determinations about the quality of the toner material.

A further object is to design an apparatus for determining electrical charge characteristics of toner material that is simple in construction and cost effective. Still further, the present invention enables one to analyze any type of toner material desired, including, for example, coarse grade toner starting materials as well as toner material with and without a carrier, i.e. so-called developers, with respect to their electrical charge properties.

In contrast to the prior art, in which the electrostatic properties of toner materials are determined by measuring the q/d ratio, only one integral dimension is determined with respect to the quantity ratio of both charges present in the toner material. It has been found that only one property is sufficient for an initial determination of the quality of toner material with respect to its electrostatic charging capacity. Moreover, in contrast to prior art methods, the method of the present invention is simpler and substantially more cost effective.

A further measuring variable for yielding information about additional characteristics regarding toner quality is obtained by recording and evaluating the distribution profiles of the toner material that has collected on the electrode. Based on such information it is even possible to draw tentative inferences about the q/d ratio of particles in the toner material. This allows further conclusions to be drawn about the electrical charging capacity of the toner material.

To evaluate even coarser starting materials with respect to their electrostatic suitability the present invention provides a further step in which the toner material is pulverized to obtain average sized grains in the range of about 1 to 50 $\mu$m, preferably 1 to 15, and which includes the further individual steps of:

introducing the toner material into a grinding chamber;

injecting at least two jets of gas at high velocity into the grinding chamber, thereby pulverizing the toner material present in the chamber;

passing the pulverized toner material through a sieve;

sifting and separating the sieved toner material in a centrifugal sifter apparatus, in particular a cyclone;

removing the toner material from the centrifugal sifter apparatus.

The apparatus of the present invention which is designed to determine the electrical charge characteristics of toner material comprises a measuring cell for receiving the toner material, together with an opening through which the toner material flows into a chamber substantially free of gas flows; further an electrode disposed within the chamber of the measuring cell, to which a voltage with a predetermined polarity is applied.

In a preferred embodiment of the present invention at least a portion of the electrode is made of a translucent or transparent (diaphanous) material, which enables the quantity of toner material that has collected on the electrode to be detected and analyzed, e.g., by means of a photomicroscope. In addition, the present invention may also include, for purposes of measuring the properties of, in particular, coarse starting material, a jet mill pulverizing apparatus for grinding down the toner material into average grain sizes ranging from about 1 to 50 $\mu$m, preferably 1 to 15 $\mu$m. The apparatus comprises:

a grinding chamber for receiving the toner material;

at least two gas nozzles opening out into the chamber for generating jets of gas that are discharged into and criss-cross in the grinding chamber;

a sieve mounted on the grinding chamber for separating the toner material ground in the grinding chamber into a residue and undersized material;

further a centrifugal sifter, in particular, a cyclone for removing the sifted undersized material.

Only minimal quantities of toner material are required for evaluating electrical charge characteristics, hence the level of efficiency of the jet mill-pulverizing apparatus is of only secondary concern. This simplifies substantially the design and construction of such a jet mill-pulverizing apparatus.

BRIEF DESCRIPTION OF THE DRAWINGS

Other aspects of the present invention will become apparent as the following description proceeds and upon reference to the drawings, in which.

DETAILED DESCRIPTION OF SPECIFIC EMBODIMENTS

Figure 1:
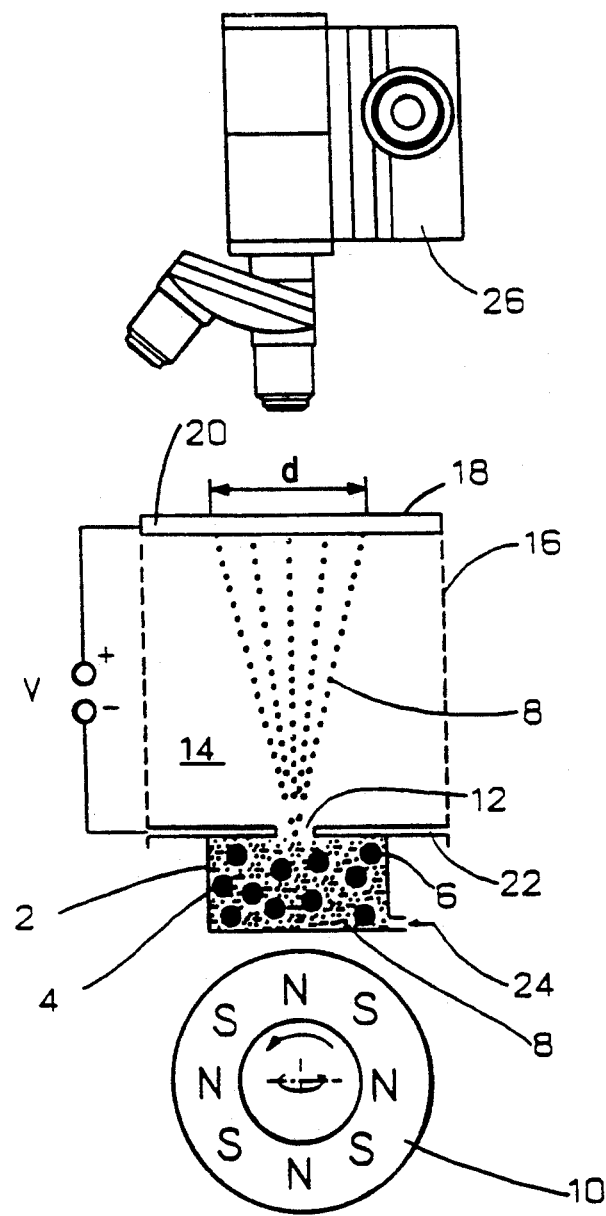
FIG. 1 is a schematic view depicting the apparatus for determining the electrostatic properties of toner materials.

The basic principle underlying a preferred embodiment of the present invention is discussed with reference to FIG. 1, which shows a measuring cell 2 into which the toner material 4 being measured is introduced. In the present example the toner material is composed of a developer with carrier particles 6 and the actual toner particles 8, i.e., a two-component-toner material. It is feasible, however, to test mono-component toner material (without a carrier), as well as any other type of toner material desired with respect to its electrostatic charge characteristics.

Usually the introduced toner material 4 is at least partially charged, or the toner material 4 is charged by the particles colliding with one another within or by colliding against the walls of measuring cell 2. For reproducing the measurement it is advantageous to charge the toner material 4 evenly. This is achieved by a magnetic device 19 disposed outside measuring cell 2, which generates a variable magnetic field by means of rotating magnetic fields disposed in a criss-cross orientation. Throughout measuring procedure, toner material 4 is activated as a result of magnetic device 10, that is, the toner material 4 is homogenized with respect to its electrostatic charge.

Measuring cell 2 is has an opening 12, the diameter of which is selected to allow at least toner particles 8 to flow through said opening 12. The toner material i.e. the toner particles 8 flow into a receiving chamber 14 which is substantially free of gas flows and is located, for example, above the measuring cell 2. Flow-free chamber 14 may be constructed as an enclosed housing (indicated by the dashed lines) with side walls 16.

FIG. 1 further shows an electrode device 18 consisting of a registration electrode 20 and a counter electrode 22 which are spaced a predetermined distance apart from one another and between which an electric field of approximately 20 to 200 kV/m is activated. In the embodiment shown in FIG. 1 electrodes 20, 22 of electrode device 18 are also constructed as walls for flow-free chamber 14, in which counter electrode 22 serves as a cover for measuring cell 2 and has an opening 12 through which the toner material flows. Due to the electric field present in flow-free chamber 14, toner particles 8 are accelerated in direct proportion to their electrical charge, e.g. toward the registration electrode, where they collect after having travelled a certain path through the electric field. Based on current technical knowledge it is known that several factors affect the transport of the toner particles. Toner particles 8 that have just exited opening 12 briefly accelerate in the electric field, then enter into a dynamic equilibrium, due to Stokes friction which is caused by the gas (air) particles (not shown in greater detail) present in flow-free chamber 14. The particles then travel at a relatively constant velocity toward registration electrode 20. The rate of critical velocity is largely determined by the quotient of the electrostatic charge and the diameter of the individual toner particles 8. Hence, toner particles 8 having a greater electrostatic charge but similar diameters traverse flow-free chamber 14 more quickly and arrive correspondingly sooner at registration electrode 20 than toner particles 6 which carry a weaker electrostatic charge.

Equally charged toner particles that repel one another, result in additional components of motion with respect to the toner particles, for example, motion perpendicular to the direction of the electric field. The greater the repellant force, the more such components predominant, i.e. they are proportional to the level of electrostatic charge of the respective toner particle. However, as was stated above, toner particles carrying a greater electrostatic charge are subject to a greater velocity component in the direction of the electric field. On the whole, therefore, the wider the dispersal of charge values or charge/diameter-values present in the toner material 4, the greater the mean diameter d of the particle collected on registration electrode 20. Experimentation has shown that the dispersal range of the toner material which has collected on registration electrode 20 represents a further qualitative measure for the evaluation of electric charge characteristics of the toner material.

In the embodiment of the present invention shown in FIG. 1 a positive voltage is initially applied to registration electrode 20, thereby attracting toner particles 8 with a negative charge which then collect on the registration electrode. It was found that the integral value relating to the quantity of toner particles which collected on registration electrode 20 over a predetermined time period is in itself sufficient for making certain determinations about the quality of toner material 4 with respect to electrical charge characteristics. For reproducing measurements it is essential that chamber 14 through which toner particles travel remain substantially free of gas or air currents. This eliminates any distorting effects during transport of the toner particles 8.

When required, the outflow of toner material 4 through opening 12 may be augmented by injecting an auxiliary gas flow 24 into measuring cell 2. In such case, however, auxiliary gas flow 24 may not enter at such a rate that it disrupts the flow-free conditions prevailing inside flow-free chamber 14. Auxiliary gas flow 24 is provided in the form of, for example, an air flow injected in pulses, in which the pulse duration falls within the range of approximately a second and a volume flow of ca. 10 m/s is obtained. Further, it is possible to augment the outflow of toner material through opening 12 (not described in greater detail) by repeatedly knocking on the measuring cell 2 or by subjecting measuring cell 2 to mechanical impulses.

Further information about the quality of toner material 4 with respect to its electrical charge characteristics can be determined when the measurement is repeated using the same toner material 4, but in which the direction of the electrical field within flow-free chamber 14 is reversed such that, e.g. a negative voltage is applied to registration electrode 20. Thus, toner particles 8 having an opposite polarity, i.e., positively-charged particles, are attracted to and collect on electrode 20. By comparing the quantity of collected toner material with the quantity collected previously when the polarity of registration code 20 was reversed, it is possible to draw significant conclusions about the electrical charge characteristics of the toner material that are a function of the difference in polarities present in the toner material 4. It was determined that, essentially, toner material in which electrical charges of one polarity clearly predominate is of a higher quality than toner material in which the proportion of positive and negative charges is essentially the same.

In a preferred embodiment of the present invention registration electrode 20 is at least partially translucent or diaphanous. This enables the toner material 4 which has collected on registration electrode 20 to be easily detected and analyzed by a photomicroscope 26, which in turn is connected to a computing device for processing the image (not shown in greater detail).

Figure 2:
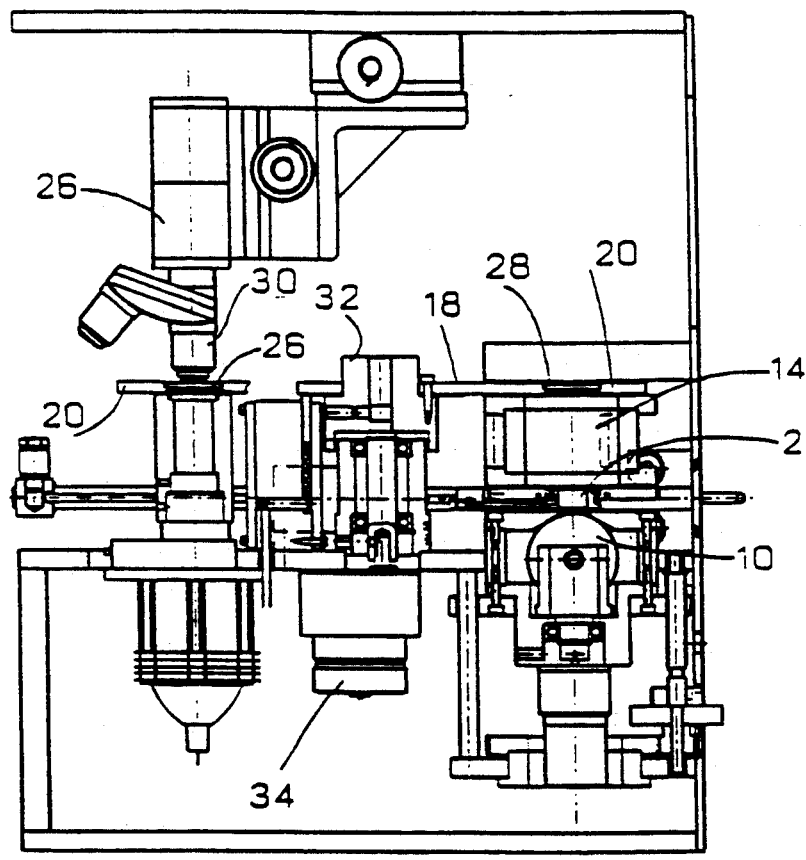
FIG. 2 is a schematic elevational view depicting an apparatus for determining the electrostatic properties of toner materials.
Figure 3:
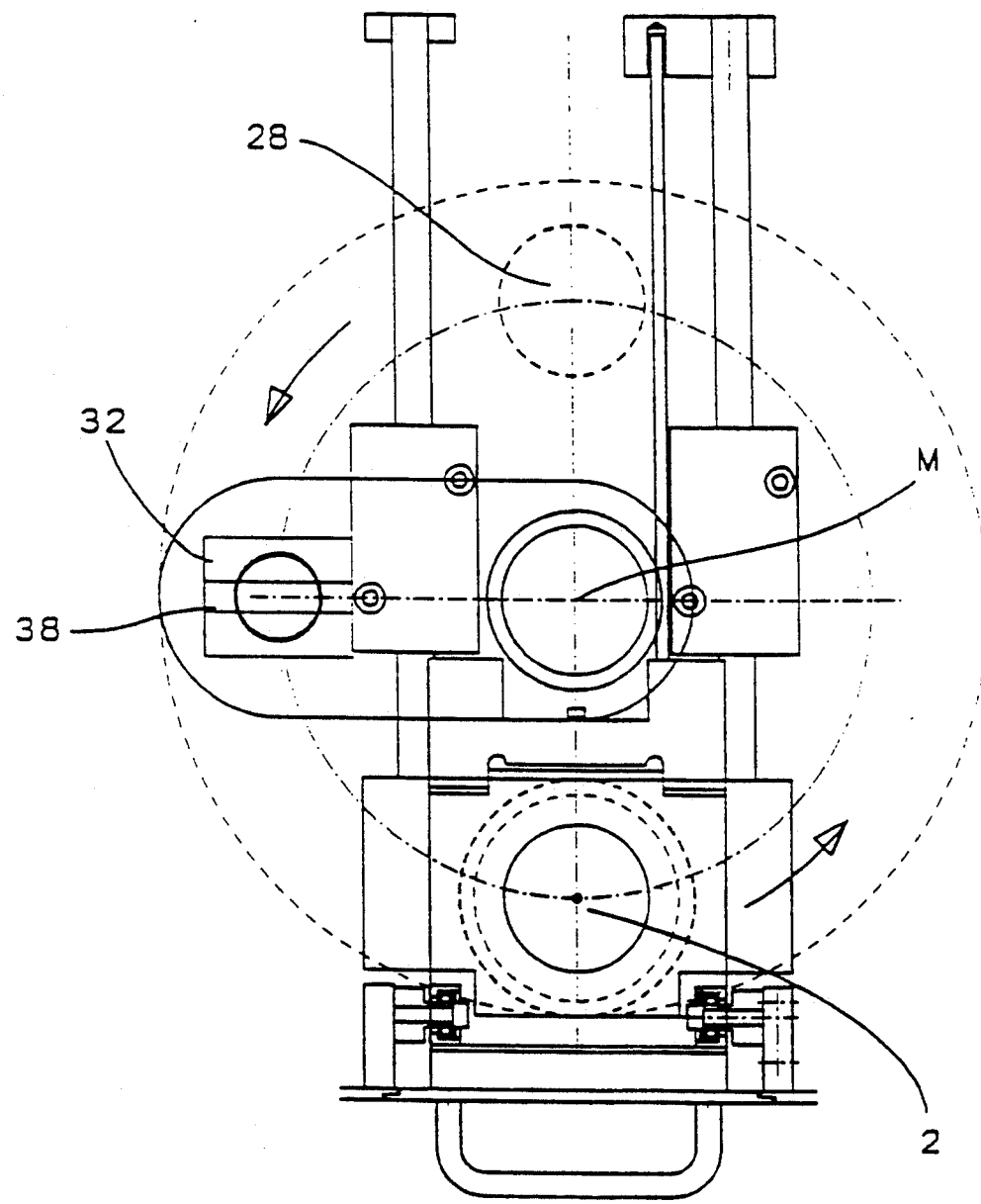
FIG. 3 is a schematic top view of the apparatus depicted in FIG. 2.

FIGS. 2 and 3 show a preferred embodiment of the present invention in greater detail, in which reference numerals in FIG. 1 refer to equivalent features in FIGS. 2 and 3. FIG. 2 clearly shows, in particular, a measuring cell 2 for receiving the toner material, over which a counter electrode 22 is mounted, a flow-free chamber 14 disposed immediately above the counter electrode, and further a registration electrode 20 with a transparent window 28. After a measurement is taken registration electrode 20, which is constructed as a rotatable electrode plate and, as is clearly seen from the plan view in FIG. 3, is rotated around a center point M in a counterclockwise direction until window 28 comes to rest under a lens 30. This enables the quantity of toner material which has collected on window 28 of registration electrode during measurement to be optically recorded.

Once the material has undergone optical analysis and, if required, the distribution of particle sizes in the toner material that has collected on window 28 has been measured, the rotatable electrode plate with window 28 is pivoted to a cleaning apparatus 32, where the collected toner material is removed or suctioned from window 28. This allows registration electrode 20 to be utilized for further measurements. The cleaning apparatus has a suction device 36 actuated by a motor 34 and which ends in a slot shaped suction nozzle 38 immediately proximate to the position to which window 28 is pivoted for cleaning registration electrode 20. It is clear that the process of cleaning the electrode is simplified substantially in the present invention as compared with prior known solutions.

Figure 4:
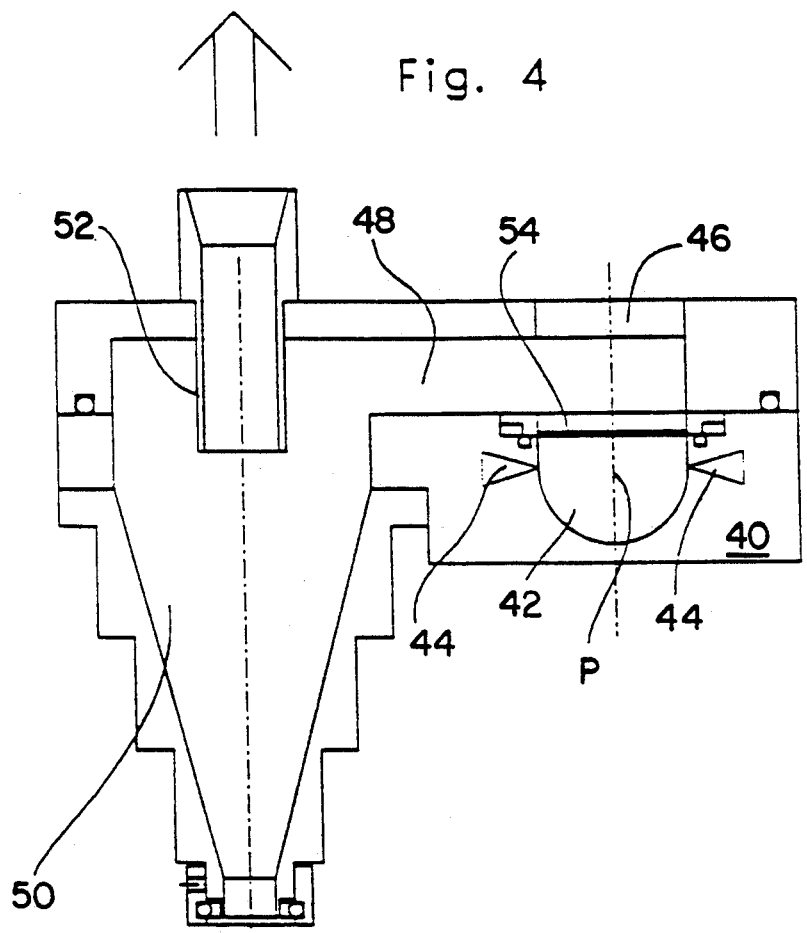
FIG. 4 is a schematic cross-sectional view of a pulverization apparatus according to the present invention.
Figure 5:
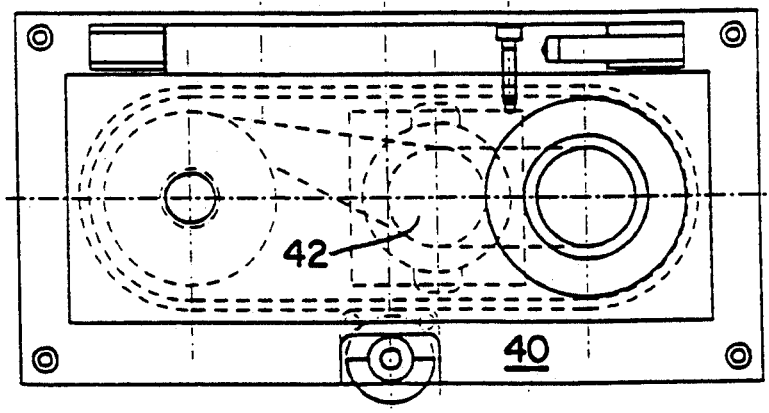
FIG. 5 is a schematic top plan view of the pulverization apparatus shown in FIG. 4.

To investigate the suitability of both finished toner material as well as coarse-grained starting material with respect to their electrostatic charging capabilities, the latter composed initially of average sized particles ranging from approximately 0.8 to 2 mm, a pulverizing apparatus 40, shown in FIGS. 4 and 5 is provided in accordance with the present invention. Pulverizing apparatus 40 consists of a semispherically shaped grinding chamber 42 into which the toner material 4 being pulverized is introduced. At least two jet nozzles 44 are mounted along the sides of and open out into grinding chamber 42. By means of nozzles 44 jets of gas are discharged into the chamber 42 at a pressure of 6 bars, respectively, and intersect inside the chamber at a point P. Pressurized jets of air blown at high velocity into grinding chamber 42 stir up the toner material contained in the chamber 42, causing the material to become pulverized through collision and deflection of the individual particles.

Outside air is drawn via a ventilator (not shown in greater detail) through a filter 46 into a channel 48 into a sifting chamber 50 and past a separator 52. Channel 48 is disposed immediately above and connected to grinding chamber 42 via a sieve 54 which has a mesh size of approximately 25 μm to 50 μm, This allows the sufficiently pulverized toner material to pass undersized through said sieve 54, from where it is introduced in an air flow passing through channel 48 to the sifting chamber 50 of a centrifugal-type sifter. In sifting chamber 50 the pulverized toner material is graded by utilizing the different rates at which the various solid particles of the toner material gravitate downward. Simultaneously, the toner material is cleaned of all dust impurities in a cyclone defined by the sifting chamber 50 and separator 52. Toner material that has been pulverized, graded and cleaned accumulates in a receptacle 56 from which it can later be removed.

The invention has been explained with reference to specific embodiments. Other embodiments will be apparent to those of ordinary skill in the art. It is therefore not intended that the invention be limited except as indicated by the appended claims.

What is claimed is:

1. A method for determining electrical charge characteristics of toner material comprising the steps of:
   introducing toner material into a measuring cell;
   enabling the toner material to flow through an opening in the measuring cell into a receiving chamber that is substantially free of gas flow;
   allowing the entering toner material to collect on an electrode disposed within the receiving chamber and to which an electric potential with a predetermined polarity is applied;
   measuring over a predetermined period of time the quantity of toner material that has entered the receiving chamber and collected on the electrode; and
   determining the electrical charge characteristics of the toner material as a function of the measuring results.

2. The method according to claim 1, further comprising the steps of:
   repeating the aforementioned steps, while applying a potential with a polarity opposite to the initial polarity to the electrode; and
   determining the electrical charge characteristics as a function of the difference in quantity of collected toner material resulting from the opposite polarities applied to the electrode, respectively.

3. The method according to claim 2, comprising prior to the repeating step, performing the additional step of:
   removing the collected toner material from the electrode.

4. The method according to claim 1, further comprising the step of:
   determining the dispersal profile of the collected toner material on the electrode as an index of the electrostatic characteristics of the toner material.

5. The method according to claim 1, in which the step of allowing the toner material to flow out is augmented by the step of injecting an auxiliary gas flow into the measuring cell.

6. The method according to claim 1, further comprising the step of:
   activating the toner material in a fluctuating magnetic field.

7. A method of determining the electric charge characteristics of toner material, comprising the steps of:
   a) introducing the toner material into a measuring cell;
   b) enabling the toner material to flow through an opening in the measuring cell into a receiving chamber that is substantially free of gas flows; thereafter c) allowing the toner material to collect on an electrode disposed within the receiving chamber, to which an electric potential with a predetermined polarity is applied;

d) measuring over a predetermined period of time the quantity of toner material that has entered the receiving chamber and collected on the electrode;

e) determining the electrical charge characteristics of the toner material as a function of the measuring results;

f) repeating steps a) to e), while applying a voltage with the opposite polarity to the electrode; and determining the electrical charge characteristics as a function of the difference in quantity of collected toner material resulting from the opposite polarities applied to the electrode, respectively.

8. The method according to claim 7, comprising prior to the aforementioned repeating step, performing the additional step of:

removing the collected toner material from the electrode.

9. The method according to claim 7 further comprising the step of:

determining the dispersal profile of the collected toner material on the electrode as an index of the electrostatic characteristics of the toner material.

10. The method according to claim 7, in which the step of allowing the toner material to flow out is augmented by the step of injecting an auxiliary gas flow into the measuring cell.

11. The method according to claim 7, further comprising the step of:

activating the toner material in a fluctuating magnetic field.

12. A method for determining the electric charge characteristics of toner material, comprising the steps of:

crushing the toner material to obtain average particle diameters of between approximately 1 $\mu$m and 50 $\mu$m according to the substeps of:

introducing the crushed toner material into a grinding chamber;

injecting at least two jets of gas into the grinding chamber with sufficient velocity to pulverize the crushed toner material contained in the grinding chamber to obtain pulverized toner material;

screening the pulverized toner material to obtain screened toner material;

sifting and separating the screened toner material in a centrifugal sifter to obtain sifted and cleaned toner material free of dust particles; thereafter removing the sifted and cleaned toner material from the centrifugal sifter; thereafter introducing the sifted and cleaned toner material into a measuring cell;

enabling the sifted and cleaned toner material to flow through an opening in the measuring cell into a receiving chamber that is substantially free of gas flows; thereafter allowing the sifted and cleaned toner material to collect on an electrode disposed within the receiving chamber while an electric potential with a predetermined polarity is applied to the receiving chamber;

measuring over a predetermined period of time the quantity of toner material that has entered the receiving chamber and collected on the electrode; and determining the electrical chamber characteristics of the toner material as a function of the results of the measuring step.

13. The method according to claim 12, further comprising the steps of:

applying a voltage with a polarity opposite to the predetermined polarity to the electrode while repeating said allowing, measuring and determining steps; and ascertaining the electrical charge characteristics of the toner material as a function of the difference in quantity of toner material collected on the electrode resulting from the applying of voltage of opposite polarities applied to the electrode.

14. The method according to claim 13 comprising, prior to the aforementioned repeating of steps, the additional step of:

removing collected toner material from the electrode.

15. The method according to claim 12 further comprising the step of:

determining the dispersal profile of the collected toner material on the electrode as an index of the electrostatic characteristics of the toner material.

16. The method according to claim 12, wherein the enabling step to permit the toner material to flow out is augmented by the step of injecting an auxiliary gas flow into the measuring cell.

17. The method according to claim 12, further comprising the step of:

activating the toner material in a fluctuating magnetic field.

18. An apparatus for determining electrical charge characteristics of toner material comprising:

a measuring cell to receive the toner material, said measuring cell having an opening through which the toner material is flows into a receiving chamber that is substantially free of gas flow; and an electrode disposed within the receiving chamber to which a potential of a predetermined polarity is applied and facing said opening so that toner material flows out of the opening straight to the electrode.

19. The apparatus according to claim 18, wherein at least a portion of the electrode is composed of a diaphanous material, and further comprising:

a photomicroscope for detecting and analyzing the quantity of toner material that has collected on the electrode.

20. The apparatus according to claim 18, further comprising:

means for generating a fluctuating magnetic field.

21. Apparatus according to claim 18, further comprising:

means for cleaning the electrode to remove the toner material that has collected on the electrode.

22. An apparatus for determining electrical charge characteristics of toner material comprising:

a receiving chamber that is substantially free of gas flows;

a measuring cell for receiving toner material and which has an opening through which toner material flows into the receiving chamber;

a diaphanous electrode disposed within the receiving chamber opposite the opening of the measuring cell so that toner material can flow out of the opening straight to the electrode; and means for applying a potential of a predetermined polarity to the electrode.

23. The apparatus according to claim 22, further comprising:
a photomicroscope for detecting and analyzing the quantity of toner material that has collected on the electrode.

24. The apparatus according to claim 22, further comprising:
a magnetic device for generating a fluctuating magnetic field.

25. The apparatus according to claim 22, further comprising:
means for cleaning the electrode to remove the toner material that has collected on the electrode.

26. An apparatus for determining electrical charge characteristics of toner material comprising:
a jet mill pulverizing means for reducing the diameter of the particles of toner material to an average side of between 1 μm and 15 μm, the jet mill pulverizing means comprising:
a grinding chamber for receiving the toner material;
at least two jet discharge nozzles that open out into the grinding chamber for generating jets of gas that are discharged into and criss-cross in the grinding chamber;
a sieve attached to the grinding chamber for separating residue from undersized particles of the toner material pulverized in the grinding chamber; and
a centrifugal sifter for grading and removing dust from undersized particles;
a receiving chamber that is substantially free of gas flows;
a measuring cell which receives the toner material and which has an opening through which the toner material flows into the receiving chamber; and
an electrode device disposed within the receiving chamber to which a voltage of a predetermined polarity is applied.

27. The apparatus according to claim 26, wherein at least a portion of the electrode comprises a diaphanous material, and further comprising:
a photomicroscope for detecting and analyzing the quantity of toner material that has collected on the electrode.

28. The apparatus according to claim 26, further comprising:
a magnetic device for generating a fluctuating magnetic field.

29. The apparatus according to claim 26, further comprising:
means for cleaning the electrode to remove the toner material that has collected on the electrode.

30. A method for determining electrical charge characteristics of toner material comprising the steps of:
pulverizing the toner material to obtain average particle diameters of approximately 1 to 50 μm, preferably 1 to 15 μm; and thereafter
introducing the toner material into a grinding chamber;
injecting at least two jets of gas at high velocity into the grinding chamber to pulverize the toner material contained in the grinding chamber;
screening the pulverized toner material;
sifting and separating the screened toner material in a centrifugal sifter, in particular a cyclone;
removing the toner material from the centrifugal sifter once it has been sifted and cleaned of all dust particles;
introducing toner material into a measuring cell;
enabling the toner material to flow through an opening in the measuring cell into a receiving chamber that is substantially free of gas flow;
allowing the entering toner material to collect on an electrode disposed within the receiving chamber and to which an electric charge with a predetermined polarity is applied;
measuring over a predetermined period of time the quantity of toner material that has entered the receiving chamber and collected on the electrode; and
determining the electrical charge characteristics of the toner material as a function of the measuring results.

31. A method of determining the electric charge characteristics of toner material, comprising the steps of:
pulverizing the toner material to obtain average particle diameters of approximately 1 to 50 μm, preferably 1 to 15 μm; and thereafter
introducing the toner material into a grinding chamber;
injecting at least two jets of gas at high velocity into the grinding chamber, thereby pulverizing the toner material contained in the grinding chamber;
screening the pulverized toner material;
sifting and separating the screened toner material in a centrifugal sifter, in particular a cyclone;
removing the toner material from the centrifugal sifter once it has been sifted and cleaned of all dust particles;
a) introducing the toner material into a measuring cell;
b) enabling the toner material to flow through an opening in the measuring cell into a receiving chamber that is substantially free of gas flows; thereafter
c) allowing the toner material to collect on an electrode disposed within the receiving chamber, to which an electric charge with a predetermined polarity is applied;
d) measuring over a predetermined period of time the quantity of toner material that has entered the receiving chamber and collected on the electrode;
e) determining the electrical charge characteristics of the toner material as a function of the measuring results;
f) repeating steps a) to e), while applying a voltage with the opposite polarity to the electrode; and
determining the electrical charge characteristics as a function of the difference in quantity of collected toner material resulting from the opposite polarities applied to the electrode, respectively.

32. An apparatus for determining electrical charge characteristics of toner material comprising:
a measuring cell to receive the toner material, said measuring cell having an opening through which the toner material is allowed to flow into a receiving chamber that is substantially free of gas flow;
an electrode disposed within the receiving chamber to which a potential of a predetermined polarity is applied and facing said opening so that toner material can flow out of the opening straight to the electrode;

a jet mill pulverizing means for reducing particles of toner material to an average diameter of between 1 μm to 50 μm, said jet mill pulverizing means further comprising:
- a grinding chamber for receiving ground toner material;
- at least two jet nozzles which open out into the grinding chamber for generating jets of gas that are discharged into a criss-cross in the grinding chamber;
- a sieve attached to the grinding chamber for separating residue from undersized particles of the ground toner material; and
- a centrifugal sifter for grading and removing dust from the undersized particles.

33. An apparatus for determining electrical charge characteristics of toner material comprising:
- a receiving chamber that is substantially free of gas flows;
- a measuring cell for receiving toner material and which has an opening through which toner material flows into the receiving chamber;
- a diaphanous electrode disposed within the receiving chamber opposite the opening of the measuring cell so that toner material can flow out of the opening straight to the electrode;
- means for applying a potential of a predetermined polarity to the electrode;
- a jet mill pulverizing means for reducing diameter of the particles of the toner material to average size of between 1 μm to 5 μm, said jet mill pulverizing means comprising:
- a grinding chamber for receiving the toner material;
- at least two jet nozzles that open out into the grinding chamber for generating jets of gas that are discharged into and criss-cross in the grinding chamber;
- a sieve attached to the grinding chamber for separating the residue from the undersized particles of the toner material pulverized in the grinding chamber; and
- a centrifugal sifter for grading and removing dust from undersized particles.

* * * * *